(12) United States Patent
Gittleman

(10) Patent No.: US 8,968,787 B2
(45) Date of Patent: Mar. 3, 2015

(54) COMPOSITION COMPRISING BIODEGRADABLE POLYMERS FOR USE IN A COSMETIC COMPOSITION

(75) Inventor: David Gittleman, Croton on Hudson, NY (US)

(73) Assignee: Micro Powders, Inc., Tarrytown, NY (US)

( * ) Notice: Subject to any disclaimer, the term of this patent is extended or adjusted under 35 U.S.C. 154(b) by 702 days.

(21) Appl. No.: 12/800,804

(22) Filed: May 24, 2010

(65) Prior Publication Data

US 2011/0287105 A1  Nov. 24, 2011

(51) Int. Cl.
| | |
|---|---|
| A61Q 19/00 | (2006.01) |
| A61Q 1/12 | (2006.01) |
| A61K 8/85 | (2006.01) |
| C08L 67/04 | (2006.01) |
| A61K 8/04 | (2006.01) |

(52) U.S. Cl.
CPC .............. *C08L 67/04* (2013.01); *A61K 8/046* (2013.01); *A61K 8/85* (2013.01); *A61Q 1/12* (2013.01); *A61Q 19/00* (2013.01); *A61K 2800/28* (2013.01); *A61K 2800/412* (2013.01)
USPC ........................................................ 424/489

(58) Field of Classification Search
None
See application file for complete search history.

(56) References Cited

U.S. PATENT DOCUMENTS

| | | | |
|---|---|---|---|
| 3,645,904 A | 2/1972 | Beach | |
| 4,650,672 A | 3/1987 | Yagita et al. | |
| 4,797,468 A | 1/1989 | De Vries | |
| 5,904,918 A | 5/1999 | Sterphone et al. | |
| 5,919,467 A | 7/1999 | Jenkins et al. | |
| 5,945,095 A | 8/1999 | Mougin et al. | |
| 6,042,839 A | 3/2000 | Lahanas et al. | |
| 6,063,366 A | 5/2000 | Sugai et al. | |
| 6,080,424 A | 6/2000 | Avalle | |
| 6,207,175 B1 | 3/2001 | Lebreton | |
| 6,309,655 B1 | 10/2001 | Minnix | |
| 6,416,751 B1 | 7/2002 | Roulier et al. | |
| 6,461,595 B1 | 10/2002 | Leo et al. | |
| 6,551,603 B1 | 4/2003 | Vinski et al. | |
| 6,555,156 B1 * | 4/2003 | Loughman | 427/2.14 |
| 6,613,359 B2 * | 9/2003 | Victor | 424/489 |
| 6,685,925 B2 | 2/2004 | Frecht et al. | |
| 6,719,985 B1 | 4/2004 | Tsubouchi et al. | |
| 6,890,522 B2 | 5/2005 | Frechet et al. | |
| 6,893,649 B2 | 5/2005 | Sasaki et al. | |
| 7,195,770 B2 | 3/2007 | Gitomer et al. | |
| 7,255,870 B2 | 8/2007 | Lennon et al. | |
| 7,410,636 B2 | 8/2008 | Collin | |
| 7,544,352 B2 | 6/2009 | Shah et al. | |
| 7,585,922 B2 | 9/2009 | Farcet | |
| 7,612,051 B2 | 11/2009 | Kamei et al. | |
| 7,628,998 B2 | 12/2009 | Shah et al. | |
| 7,632,873 B2 | 12/2009 | Mougin | |
| 7,670,999 B2 | 3/2010 | Sebillotte-Arnaud et al. | |
| 7,682,622 B2 | 3/2010 | Horino | |
| 2004/0146540 A1 * | 7/2004 | Ueda et al. | 424/401 |
| 2006/0280801 A1 | 12/2006 | Kronenthal | |
| 2007/0078290 A1 | 4/2007 | Esenaliev | |
| 2010/0015240 A1 | 1/2010 | Biggs | |

OTHER PUBLICATIONS

Nykamp et al. (International Journal of Pharmaceutics 2002, 242:79-86).*
Dendukuri et al. (Nature Materials May 2006:365-369).*
Champion et al. (Journal of Controlled Release 2007, 121:3-9).*
Ikada et al. (Macromol. Rapid. Commun. 2000; 21:117-132).*

* cited by examiner

*Primary Examiner* — Ernst V Arnold
(74) *Attorney, Agent, or Firm* — Schmidt LLC

(57) ABSTRACT

The present invention relates to certain novel polymer powder compositions suitable for personal care and cosmetic compositions. The present invention also relates to cosmetic compositions comprising such novel polymer powders. The present invention also relates to processes for manufacturing the polymer powders, methods of making cosmetic and personal care compositions and the use of such cosmetic compositions in topical applications.

31 Claims, No Drawings

COMPOSITION COMPRISING BIODEGRADABLE POLYMERS FOR USE IN A COSMETIC COMPOSITION

FIELD OF INVENTION

The present invention relates to certain novel polymer powder compositions suitable for personal care and cosmetic compositions. The present invention also relates to cosmetic compositions comprising such novel polymer compositions. The present invention further relates to processes for micronizing polymer pellets, methods of making cosmetic and personal care compositions and the methods of using such cosmetic compositions in topical applications.

More particularly, the present invention relates to cosmetic compositions, including fine particle cosmetic products, loose and packed cosmetic powders, foundations, eye shadows, scrub soaps, scrubs, exfoliating agents, creams, liquids, gels, lotions and compositions suitable for keratin materials made from micronized biodegradable polymers. The compositions according to the invention are intended more particularly for the keratin materials of human beings, such as the skin (including the scalp), the nails and keratin fibers, and/or mucous membranes.

BACKGROUND

Prior Art Cosmetics

Cosmetics have been around since Biblical times. Over the years cosmetics have been developed in many different formulations and in many different forms whether as a powder, liquid, gel or cream. These different formulations and forms have been used for a host of topical uses.

Cosmetic powders have been long known and commercially available in both loose and pressed powder form. Cosmetic powders have been used for a variety of topical application such to the face, lips, around the eyes, nails, scalp and other body locations. The uses of these cosmetic powders include reducing, inhibiting or preventing moisture loss from the skin for an extended period of time; absorbing excess sebum/oil from the skin to reduce shine and filling in blemishes.

Cleansing compositions have also been around for many years whether in powder, liquid or cream form. Cleansing the skin is also very important especially for the care of the face. Cleansing must be as thorough as possible because greasy residues, such as excess sebum, dead skin cells, and remnants of cosmetic products used daily and make-up products accumulate in the folds of the skin and can block the pores of the skin and result in blemishes.

Various forms of cosmetic compositions for cleaning the skin have been known for years. For example, U.S. Pat. No. 3,645,904 discloses a skin cleaner having plastic synthetic resin material in a fine state of comminution so as to impart a scrubbing or mechanical detersive action thereto.

Similarly, U.S. Pat. No. 6,063,366 discloses a cosmetic composition comprising disintegrating granules that facilitate the circulation of the blood to improve a complexion. The disintegrating granules are composed of synthetic polymers such as polyethylene, polystyrene, polyester, polyvinyl chloride, polyamide, polypropylene, and nylon in a silicone solvent wherein the disintegrating granules in the cosmetic composition have a compression strength of 0.002 to 0.1 kgf/mm$^2$ and a granule size of 100 to 2,000 microns.

U.S. Pat. No. 6,309,655 discloses a cosmetic composition comprising self-heating, self-indicating disintegrating granules comprised of water-insoluble synthetic polymer and a colorant, which gives users indications of the length of time the composition has been applied and the degree of mixing when in use.

U.S. Pat. No. 7,195,770 discloses a body scrub wherein the cosmetic composition comprises crushed up basalt. Though basalt is a natural ingredient it is a mineral and not a biodegradable polymer.

U.S. Pat. No. 7,585,922 discloses polymer particles dispersions in a silicone medium and cosmetic compositions made therefrom. However, the object of this patent was to stabilize the polymer dispersion without the use of a stabilizing polymer. This was accomplished by modifying the physicochemical properties of the dispersion, and thus of the composition comprising it, by appropriately selecting the monomers and the silicone medium of which it is composed. The polymer particle dispersion of this patent comprised a copolymer that comprises at least one first block that is soluble in the silicone medium and at least one second block that is insoluble in the silicone medium.

U.S. Pat. No. 4,508,634 discloses an aqueous skin cleaner composition comprising propylene carbonate suitable for removing paint, grease, dirt and other foreign materials from the skin.

As will be seen none of the prior art discloses the present invention.

Biodegradable Polymers

In recent years, interest in protecting the environment by not only using products made from natural renewable resources, but also products that decompose into environmentally friendly constituents has been steadily and rapidly increasing. Green movements, initiatives and regulations have sprung up in almost every developed country. Consumers, in particular, have also expressed their desire for products that are environmentally friendly while providing the same results that products made from synthetic materials. This desire by consumers for environmentally friendly products has spread to cosmetics and health care products.

To help facilitate consumer preferences for environmentally friendly products several organizations have begun certifying products meeting environmentally friendly standards. One such organization is Ecocert (http://www.ecocert.com). Ecocert certifies that the raw materials that go into cosmetic and health care products are of natural or organic origin. Certification by Ecocert has become increasingly important to consumers, especially consumers of cosmetic and personal care products. In order to obtain Ecocert certification, a product must meet the exacting demands set forth by Ecocert. (http://www.ecocert.com/Les-etapes-de-la-certification-en.html). Thus, certification by Ecocert guarantees consumers that they are buying environmentally friendly cosmetics.

However, consumer preferences for environmentally friendly products can be hindered by the higher cost of such environmentally friendly products as compared to synthetically derived products. Likewise, such preferences for environmentally friendly products can be also frustrated if environmentally friendly products do not produce the desired results as compared to the synthetically derived product.

Therefore, there has been a long felt need for environmentally friendly cosmetic and personal care products that have comparable cost as synthetically derived products now being offered for sale while still maintaining the desired efficacy and results. Such products are highly desirable because consumers want a product that is environmentally friendly, will not deplete scarce and limited resources such as petroleum, has comparable costs as compared to non-environmentally friendly products and are not toxic to the skin while still providing the necessary skincare result.

Over the years biodegradable polymers such as polylactic acid (PLA) have been employed in several products. Because polylactic acid (PLA) has high transparency, toughness, and is easily hydrolyzed in the presence of water, blends of stereocomplexes of polylactic acid (PLA) have been woven into shirts, microwavable trays, hot-fill applications and even engineering plastics.

Because polylactic acid (PLA) is 100% biodegradable it can also be employed in the preparation of bioplastics, useful for producing loose-fill packaging, compost bags, food packaging, and disposable tableware.

In addition, because polylactic acid (PLA) easily decomposes and is absorbed in a living body without exerting toxicity it has been used in vivo. For example, polylactic acid (PLA) is currently used in a number of biomedical applications, such as sutures, stents, dialysis media, tissue scaffolds and drug delivery devices.

However, none of the prior art discloses micronizing polylactic acid (PLA) pellets into micro granules to make them suitable for topical applications and then using it topically in micronized form. Further, the prior art does not disclose the use of micronized polymers that are substantially biodegradable, that are made from annual renewable resources and that provide efficacious results for use in a skincare product. Likewise, none of the prior art discloses the use of micronized polylactic acid (PLA) in cosmetic compositions, and more specifically as a filler in a powder cosmetic composition and as the abrasive particles in a scrub cosmetic composition.

SUMMARY OF THE INVENTION

The present inventor has discovered, surprisingly, novel methods for micronizing polylactic acid (PLA) to make it suitable for topical applications.

The present inventor has also discovered, surprisingly, novel polylactic acid (PLA) powder compositions in micronized form suitable for topical use, including use in skincare products, loose and packed cosmetic powders, cleansing scrubs and other cosmetic compositions.

It is another object of the invention to provide processes for caring for the keratin materials of human beings, comprising the application of a composition containing the polymer compositions defined above to the keratin materials.

It is yet another object of the present invention to provide a process for making cosmetic compositions using the micronized polylactic acid (PLA) powder compositions.

The cosmetic powder composition of this invention may be any suitable cosmetic powder composition for application to any suitable area of skin, such as for application to the face, lips, nose, around the eye, the scalp, or any other suitable body area. The cosmetic powder compositions of the present invention may be free flowing, loose powder compositions or pressed powder compositions.

The environmentally friendly powder compositions of the present invention are designed to provide increased slip properties and enhanced texture to the cosmetic and personal care formulations. The micronized polylactic acid (PLA) powder compositions of the present invention are ideally suited as binders in pressed powder formulations.

Further, the cosmetic compositions comprising the micronized biodegradable polymers afford good cosmetic properties while being made from annual renewable resources that degrade into environmentally friendly constituents and that have comparable manufacturing costs as compared to synthetically derived products. The compositions of the present invention gives cosmetic compositions that are is easy to apply to the skin surface and provide good feel.

More specifically, the cosmetic compositions of the present invention comprise micronized polylactic acid (PLA) particles of various sizes depending on the intended application. These compositions may also comprise other additives that are normally found in cosmetic compositions, again depending on the intended application.

These and other objects of the present invention will become more readily apparent from consideration of the following summary and detailed description. Further areas of applicability of the present invention will become apparent from the detailed description provided hereinafter. It should be understood that the detailed description, while indicating the preferred embodiment of the invention, are intended for purposes of illustration only and are not intended to limit the scope of the invention.

DETAILED DESCRIPTION OF EXEMPLARY EXAMPLES

The present invention involves the development of novel biodegradable polymer powder in micronized form suitable for use in topical applications such as use cosmetic and personal care compositions. The novel biodegradable polymer powder compositions and polymer scrub compositions of the present invention afford good cosmetic properties while being made from annual renewable resources, fully degrade into environmentally friendly constituents and have comparable manufacturing costs as compared to synthetically derived products.

The biodegradable polymers for ultimate use in the compositions of the present invention are commercially available and may be obtained from various chemical manufacturers in large pellet form. One biodegradable polymer of the present invention is polylactic acid (PLA). PLA is commercially available in pellet form and can be obtained, for example, from NatureWorks LLC (Minnetonka, Minn.) under the trade name NatureWorks®.

Polylactic acid (PLA) can also be made by processes well known in the art. For example, polylactic acid (PLA) can also be made by polycondensation of lactic acid. Using this process a polymer with a relatively low molecular weight is obtained with the elimination of water. A copolymer having low molecular weight is obtained on condensing a mixture of lactic acid and glycolic acid. In most cases these polymers are not usable for many applications, and in particular, are not usable for application as a biodegradable polymer. Thus further processing is required.

Polylactic acid (PLA) having a higher molecular weight can be virtually exclusively obtained by decomposing the above-mentioned low-molecular polylactic acid by thermal treatment, a stable compound consisting of two lactic acid radicals being obtained. A high-molecular polylactic acid can be obtained by polymerizing this compound, termed lactide, provided this starting compound does not contain any impurities which interfere with the progress of the polymerization.

Therefore, recrystallization of this starting substance at least once and, preferably, several times is recommended by the prior art. However, such a recrystallization results in considerable lactide losses.

U.S. Pat. No. 4,797,468 discloses a more efficient process for creating purified polylactic acid (PLA) without the large lactide loss. This result is obtained by polymerizing the lactide optionally in the presence of other polymers or monomers followed by decomposition of the low-molecular polylactic acid thus obtained. The crude lactide is dissolved in an organic solvent which is liquid under the given conditions and which is not miscible with water, and this solution is then extracted with water in which a basic substance is dissolved which is not soluble, or only very sparingly soluble in the said organic solvent, after which the lactide is isolated from the organic solvent layer and (optionally after further purification) is used for polymerization or copolymerization to a high-molecular polylactic acid or copolymer thereof.

This extraction method removes precisely those impurities occurring in the crude lactide which apparently influence the course of the polymerization and in one way or another affect the chain length without large losses being produced in relation to the lactide usable and available for the polymerization.

Micronizing the Biodegradable Polymers

The polylactic acid (PLA) pellets of the present invention whether obtained commercially or produced using any known method for obtaining such polymers are too large and cannot be used for the powder and cosmetic compositions of the present invention.

The inventor has found, surprisingly, processes for micronizing the polylactic acid (PLA) pellets to make them suitable for use in topical applications of the present invention.

For use in the powder compositions and cosmetic compositions a polylactic acid (PLA) particle size greater than 120 mesh as determined using the ASTM E11 test method is preferably used. The large polylactic acid (PLA) pellets can be processed to the required size according to methods generally known in the art, including by grinding it cryogenically on a disk mill (mechanical grinding).

For use in the powder compositions and cosmetic compositions with a polylactic acid (PLA) particle less than 120 mesh the polylactic acid (PLA) pellets can be processed to the required average particle size according to methods generally known in the art, including via an air jet mill.

A person skilled in the art will be able to determine the necessary parameters for processing the polylactic acid (PLA) into the necessary particle size by methods generally known in the art, including by disk or air jet milling without undue experimentation. In addition, there are several commercial enterprises that have toll processing services that can be contracted to micronize the large polylactic acid (PLA) pellets to suitable sizes for the powder and cosmetic compositions of the present invention.

Polymer Powder Compositions of the Invention

Once the polylactic acid (PLA) is micronized it can be incorporated into powder compositions suitable for use in cosmetic compositions. The powder compositions of the present invention are preferably ultimately formulated into powder and skincare compositions, but can also be formulated into a wide variety of product types, including rinses, hand and body lotions, mousses, gels, lotions, tonics, sprays, shampoos, conditioners, facial moisturizers, sunscreens, anti-acne preparations, topical analgesics, mascaras, and the like.

The micronized powder compositions of the present invention can be in an amount from 0.5% to 100% by weight micronized PLA powder. One or more additional components can be added with the only caveat being that they are cosmetically compatible with the PLA powder. These additives can be added in a net amount of from 0.1% to 99.5% and more preferably in the amount of 10% to 50%. Preferred additives include waxes, polymers and binders. Preferred waxes include natural waxes, even more preferably copernica cerifera wax.

When an additive is to be added to the micronized polymer powder it is preferable to make a homogeneous mixture or blend. When one or more waxes are to be used in the composition with micronized polylactic acid (PLA) it is preferable to melt the wax or waxes and the micronized polylactic acid (PLA) polymer together then micronizing the resulting mixture to provide a homogeneous blend.

Cosmetic Compositions of the Invention

The micronized powder compositions of the present invention can be formulated into products for topical administration, including into powder cosmetics or scrubs.

The powder cosmetic compositions of the present invention preferably contain micronized polylactic acid (PLA) powder in an amount of from 1% to 30%, more preferably from 5 to 10% by weight.

The powder compositions according to the invention can have particle size (or number-average particle size) which can range in particular from about 0.1 to about 44 microns, preferably with a mean particle size of 5 to 20 microns with a maximum particle size of 44 microns, and more preferably with a mean particle size of 8 to 12 microns with a maximum particle size of 31.11 microns. The particle size ranges include all specific values and subranges therebetween. The particle size may be measured with the machine "Microtrac X100 & SRA 150" from Leeds-Northrup as per ASTM D4464 standard.

Particle size above 44 microns the powder will not have a good sensation or texture and the user will "feel" the powder particles upon application which will lead to discomfort.

The scrub compositions according to the invention preferably contain polylactic acid (PLA) in an amount of from 1% to 10%, more preferably from 3% to 7.5%, and even more preferably 3% to 5% by weight.

The scrub compositions according to the invention have particle size (or number-average particle size) which can range in particular from about 140 mesh to about 14 mesh, preferably from 120 mesh to 20 mesh, and more preferably from 100 mesh to 20 mesh. The particle size ranges include all specific values and subranges therebetween. The particle size is determined using the ASTM E11 standard with an Alpine Sieve. The particle size chosen will depend on the intended application and the abrasive effect desired. Particle sizes above the listed ranges will produce too much abrasive effect and lead to irritation of the skin of the user. Particle sizes below the listed range value will be too small to provide the necessary abrasive effect required for the user. Thus, the applicant has found the listed ranges to be ideally suited for cosmetic scrub compositions of the present invention.

Other Materials and Additives

Other materials may be present in the compositions of the present invention. In the selection of ingredients in the compositions of the present invention, it is contemplated that materials will be utilized that are compatible, both chemically and physically, with the biodegradable polymers. Such materials include, but are not limited to, cosmetically acceptable diluents or carriers, binders, pigments, pharmacological agents, surfactants, excipients and fillers.

The powder cosmetic compositions herein also comprise one or more cosmetic base powder components selected from pigments, fillers and binders, and mixtures thereof. It will be appreciated that many of the conventional components of powder cosmetic compositions have more than one functionality and they can therefore be classified under more than one functional types.

Suitable pigments for use herein can be inorganic and/or organic. Also included within the term pigment are materials having a low color or luster such as matte finishing agents, and also light scattering agents. Examples of suitable pigments are iron oxides, acylglutamate iron oxides, ultramarine blue, D&C dyes, carmine, and mixtures thereof.

The total concentration of high luster coloring agents in the powder cosmetic compositions may be from about 0.01% to about 30% by weight, preferably from about 1% to about 20%, and more preferably from about 1% to about 15% by weight of the total composition, the exact concentration being dependent to some extent upon the specific mixture of pigments selected to achieve the desired shades. The preferred compositions contain from about 0.1% to about 5% by weight of iron oxides.

Also suitable for use herein especially from the viewpoint of moisturization, skin feel, skin appearance and emulsion compatibility are treated pigments. Pigments can be treated with compounds such as amino acids (e.g., lysine), silicones, lauroyl, collagen, polyethylene, lecithin and ester oils. The more preferred pigments are the silicone (polysiloxane) treated pigments.

The powder compositions can also include at least one matte finishing agent. The function of the matte finishing agent is to hide skin defects and reduce shine. Such cosmetically acceptable inorganic agents, i.e., those included in the CTFA Cosmetic Ingredient Dictionary, Third Ed., as silica, hydrated silica, silicone-treated silica beads, mica, talc, polyethylene, calcium silicate, titanium dioxide, bentonite, hectorite, kaolin, chalk, diatomaceous earth, attapugite, zinc oxide and the like may be utilised. Of particular usefulness as a matte finishing agent is low luster pigment such as titanated mica (mica coated with titanium dioxide) coated with barium sulphate. Of the inorganic components useful as a matte finishing agent, low luster pigment, talc, hydrated silica, kaolin, titanium dioxide and mixtures thereof are particularly preferred.

Materials suitable for use herein as light-scattering agents can be generally described as spherical shaped inorganic materials having a particle size of up to about 100 microns, preferably from about 5 to about 50 microns, for example spherical silica particles.

The powder compositions herein can also comprise one or more filler materials. Examples of suitable fillers include talc, rice starch and/or bismuth oxychloride, preferably talc. It may also be desirable to include a dry binder in the powder compositions of the invention. Examples of suitable dry binders include magnesium stearate, zinc stearate, calcium stearate, lithium stearate, and mixtures thereof. Preferred ranges of the filler materials is from about 5% to about 90% by weight, preferably from about 30% to about 80%, and more preferably from about 60% to about 80% by weight of the total composition.

In addition, the cosmetic compositions of the invention may also comprise any additive usually used in cosmetics and personal care compositions according to the present invention, such as antioxidants, fillers, preserving agents, fragrances, neutralizing agents, thickeners, cosmetic or dermatological active agents such as, for example, emollients, moisturizers, vitamins and sunscreens, and mixtures thereof. Preferred ranges of additives is from about 0.5% to about 20% by weight, preferably from about 1% to about 10%, and more preferably from about 2% to about 5% by weight of the total composition.

The scrub compositions of the present invention can also include any cosmetically acceptable agent that is compatible, both chemically and physically, with the biodegradable polymers. Such materials include, but are not limited to, cosmetically acceptable diluents or carriers, binders, pigments, pharmacological agents, surfactants, excipients and fillers. Preferred ranges for the cosmetically acceptable agent is from about 5% to about 90% by weight, preferably from about 30% to about 80%, and more preferably from about 60% to about 80% by weight of the total composition.

Examples of possible additives can be found in U.S. Pat. Nos. 7,632,873; 7,670,999; 7,410,636 and 7,351,418 all of which are incorporated by reference in their entirety herein.

Surfactants whether foaming or non-foaming may also be employed in the compositions of the present invention. The foaming surfactants used may be nonionic, anionic, amphoteric or zwitterionic surfactants. A person skilled in the art will be able to choose a surfactant to meet the need of the composition without undue experimentation. Further, examples of foaming surfactants can be found in U.S. Pat. No. 7,655,702 which is specifically incorporated by reference in its entirety herein. Preferred ranges for the surfactants is from about 1% to about 60% by weight, preferably from about 10% to about 50%, and more preferably from about 20% to about 40% by weight of the total composition.

In addition, the cosmetic compositions according to the present invention, can include ingredients commonly used in the classical external skin care compositions, skin cleansing compositions, cosmetic compositions and massaging compositions, for example, oily substances, anti-melanogenic agents, sebum secretion inhibitors, blood circulation-facilitating agents, softeners, surfactants, keratin protecting agents, thickeners, antiseptics, pH adjusters, perfume bases, colorants, medicinally-effective agents, solvents, cosmetic or dermatological active agents such as, for example, emollients, moisturizers, vitamins and sunscreens, and mixtures, may be suitably incorporated in addition to the above-described components so far as no detrimental influence is thereby imposed on the effects of the present invention. Preferred ranges for theses additives is from about 1% to about 60% by weight, preferably from about 10% to about 50%, and more preferably from about 20% to about 40% by weight of the total composition.

Other optional ingredients which can be included in the compositions of the invention include preservatives in amounts generally about 1% or less by weight. Suitable preservatives include methylparaben, propylparaben, imidazolidimyl urea, phenoxyethanol, and mixtures thereof. The compositions may also contain fragrances, sunscreens and chelating agents.

Needless to say, a person skilled in the art will take care to select the optional additional additives and/or the amount thereof such that the advantageous properties of the composition according to the invention are not, or are not substantially, adversely affected by the addition envisaged.

Manufacture of the Cosmetic Compositions

The composition according to the invention may be manufactured by the known processes generally used in cosmetics or dermatology. For example, the compositions may be prepared by mixing the materials by any conventional means or any means known to one of ordinary skill in the art including, but not limited to, mechanical mixers.

The following examples will more fully illustrate the embodiments of this invention. It will be understood that the following examples are illustrative and not meant to limit the invention in any way. All parts, percentages and proportions referred to herein and in the appended claims are by weight unless otherwise illustrated.

EXAMPLES

Example 1

Pressed Powder

A pressed powder compositions comprising polylactic acid (PLA) with a mean particle size of 8.0 to 12.0 microns and the ingredients listed below was made according to the following:

| Product Name | INCI Name | % W/W | Supplier |
|---|---|---|---|
| Phase A | | | |
| Talc Micro Ace P-2 | Talc | 40.00 | Presperse LLC (Somerset, NJ) |
| Unipure Yellow LC182 Oxide | Iron Oxide | 1.75 | Sensient Cosmetic Techs. (South Plainfield, NJ) |
| Unipure Brown LC881 Oxide | Iron Oxide | 1.20 | Sensient Cosmetic Techs. (South Plainfield, NJ) |
| Unipure Black LC989 Oxide | Iron Oxide | 0.10 | Sensient Cosmetic Techs. (South Plainfield, NJ) |
| Potassium Sorbate | Potassium Sorbate | 0.20 | Lotioncrafter LLC. (Olga, WA) |
| Tetrasodium EDTA | Tetrasodium EDTA | 0.05 | Lotioncrafter LLC. (Olga, WA) |
| Protachem LL | Lauroyl Lysine | 2.00 | Protameen Chemicals Inc. (Totowa, NJ) |
| Talc Micro Ace P-2 | Talc | 36.40 | Presperse LLC (Somerset, NJ) |
| Phase B | | | |
| Sericite SL-012 | Mica (and) Methicone | 9.00 | Presperse LLC (Somerset, NJ) |
| EcoSoft 608 | Polylactic Acid | 5.00 | Micro Powders, Inc. (Tarrytown, NY) |
| Phase C | | | |
| Protachem ISP | Isotearyl Palmitate | 3.55 | Protameen Chemicals Inc. (Totowa, NJ) |
| Vitamin E-Acetate | DL-alpha-tocopheryl acetate | 0.10 | BASF Corp. (Florham Park, NJ) |
| Barguard CP | Caprylyl Glycol, Phenoxyethanol, Hexylene Glycol | 0.75 | Paradigm Research Science |

The ingredients listed for Phase A were combined in the order listed above. The mixture was passed through a micro-pulverizer twice such as a Hammermill with a 0.020 or 0.035 herringbone screen or a 4" Jetmill @ 40 g/min (2.4 kg/hr). The powder phase was drawn down to check for streaking. If needed, the powder composition is re-pulverized to ensure uniformity of phase/color. The Phase B materials are then added to the Phase A composition and the combined mixture is blended well with a CBM Mixer (6 qt, tumble speed 35, impeller speed 3500) for 1 minute until evenly dispersed.

The polylactic acid (PLA) used in the above formulation has a mean particle size of 8.0 to 12.0 microns as measured using a Microtrac device and the ASTM D4464 test method.

The Phase C materials are pre-mixed separately and then added to the Phase AB composition and the resulting composition is blended well with a CBM Mixer (6 qt, tumble speed 35, impeller speed 3500) for 1 minute until evenly dispersed.

The resulting powder compositions are environmentally friendly and have a good slip resistance and texture. The resulting powder compositions have many and diverse cosmetic applications, including use as foundations, eye shadow, blushes, skincare preparations, mascaras, creams, gels, and lotions.

Example 2

Loose Face Powder

A loose face powder compositions comprising polylactic acid (PLA) with a mean particle size of 8.0 to 12.0 microns and the ingredients listed below was made according to the following:

| Product Name | INCI Name | % W/W | Supplier |
|---|---|---|---|
| Phase A | | | |
| Talc Micro Ace P-2 | Talc | 44.04 | Presperse LLC (Somerset, NJ) |
| Unipure Red LC381 Oxide | Iron Oxide | 0.73 | Sensient Cosmetic Techs. (South Plainfield, NJ) |
| Unipure Yellow LC182 Oxide | Iron Oxide | 1.23 | Sensient Cosmetic Techs. (South Plainfield, NJ) |
| Unipure Black LC989 Oxide | Iron Oxide | 0.65 | Sensient Cosmetic Techs. (South Plainfield, NJ) |
| Phase B | | | |
| Sericite SL-012 | Mica (and) Methicone | 5.00 | Presperse LLC (Somerset, NJ) |
| EcoSoft 608 | Polylactic Acid | 10.00 | Micro Powders, Inc. (Tarrytown, NY) |
| Talc Micro Ace P-2 | Talc | 30.00 | Presperse LLC (Somerset, NJ) |
| Phase C | | | |
| Dermol 258 | C12-C15 Alkyl Octanoate | 1.75 | ALZO Int'l (Sayreville, NJ) |
| BHT | Butylated hydroxytoluene | 0.05 | Many |
| Barguard CP | Caprylyl Glycol, Phenoxyethanol, Hexylene Glycol | 0.75 | Paradigm Research Science |
| Phase D | | | |
| PresPearl Elegant Gold | Mica (and) Titanium Oxide (and) Iron Oxide | 4.00 | Presperse LLC (Somerset, NJ) |
| PresPearl Ruby Red | Mica (and) Iron Oxide | 1.30 | Presperse LLC (Somerset, NJ) |
| PresPearl | Mica (and) Titanium Dioxide (and) Iron Oxide | 0.50 | Presperse LLC (Somerset, NJ) |

The ingredients listed for Phase A were combined in the order listed above. The mixture was passed through a micro-pulverizer twice such as a Hammermill with a 0.020 or 0.035 herringbone screen or a 4" Jetmill @ 40 g/min (2.4 kg/hr). The powder phase was drawn down to check for streaking. If needed, the powder composition is re-pulverized to ensure uniformity of phase/color. The Phase B materials are then added to the Phase A composition and the combined mixture is blended well with a CBM Mixer (6 qt, tumble speed 35, impeller speed 3500) for 1 minute until evenly dispersed until evenly dispersed.

The polylactic acid (PLA) used in the above formulation has a mean particle size of 8.0 to 12.0 microns as measured using a Microtrac device and the ASTM D4464 test method.

The Phase C materials are pre-mixed. Slight heat may be required to ensure that the BHT is dissolved in the phase. However, in no event, should the Phase C composition be heated above 40 degrees Celsius. The Phase C composition is then added to the Phase AB composition and the resulting composition is blended well until the materials are evenly dispersed. The Phase D materials are then added to the Phase ABC composition and the composition is blended well in a CBM Mixer (6 qt, tumble speed 35, impeller speed 3500) for 1 minute until evenly dispersed until the materials are evenly dispersed.

The resulting powder compositions are environmentally friendly and have a good slip resistance and texture. The resulting powder compositions have many and diverse cosmetic applications, including use as foundations, eye shadow, blushes, skincare preparations, mascaras, creams, gels, and lotions.

Example 3

Loose Mineral Powder

A loose mineral powder comprising polylactic acid (PLA) with a mean particle size of 8.0 to 12.0 microns and the ingredients listed below was made according to the following:

| Product Name | INCI Name | % W/W | Supplier |
|---|---|---|---|
| Phase A | | | |
| Sericite PHN | Mica | 62.94 | Presperse LLC (Somerset, NJ) |
| Satin B-UVS | Bismuth Oxychloride | 15.00 | Presperse LLC (Somerset, NJ) |
| Unipure Yellow LC182 Oxide | Iron Oxide | 1.73 | Sensient Cosmetic Techs. (South Plainfield, NJ) |
| Unipure Red LC381 Oxide | Iron Oxide | 1.28 | Sensient Cosmetic Techs. (South Plainfield, NJ) |
| Unipure Black LC989 Oxide | Iron Oxide | 0.60 | Sensient Cosmetic Techs. (South Plainfield, NJ) |
| Zinc Stearate | Zinc Stearate | 2.00 | Sun Ace Kakoh Ltd (Singapore) |
| Phase B | | | |
| Sericite SL-012 | Mica (and) Methicone | 5.00 | Presperse LLC (Somerset, NJ) |
| EcoSoft 611 | Polylactic Acid (and) Copernica Cerifera (Caranauba) Wax | 10.00 | Micro Powders, Inc. (Tarrytown, NY) |
| Phase C | | | |
| Ceraphyl 368 | Ethylhexyl Palmitate | 0.50 | International Specialty Products (Wayne, New Jersey) |
| Dermol 258 | C12-C15 Alkyl Octanoate | 0.35 | ALZO Int'l (Sayreville, NJ) |
| Barguard CP | Caprylyl Glycol, Phenoxyethanol, Hexylene Glycol | 0.75 | Paradigm Research Science |

The ingredients listed for Phase A were combined in the order listed above. The mixture was passed through a micropulverizer twice such as a Hammermill with a 0.020 or 0.035 herringbone screen or a 4" Jetmill @ 40 g/min (2.4 kg/hr). The powder phase was drawn down to check for streaking. If needed, the powder composition is re-pulverized to ensure uniformity of phase/color. The Phase B materials are then added to the Phase A composition and the combined mixture is blended well with a CBM Mixer (6 qt, tumble speed 35, impeller speed 3500) for 1 minute until evenly dispersed. until evenly dispersed.

Ecosoft 611 used in the above formulation is a combination of polylactic acid and prime yellow carnauba wax #1. These polymers are melted together then micronized in order to provide a more homogeneous blend of these two environmentally friendly "green" polymers. EcoSoft 611 has a mean particle size of 8.0 to 12.0 microns as measured using a Microtrac device and the ASTM D4464 test method.

The Phase C materials are pre-mixed separately and then added to the Phase AB composition and the resulting composition is blended well with a CBM Mixer (6 qt, tumble speed 35, impeller speed 3500) for 1 minute until evenly dispersed.

The resulting powder compositions are environmentally friendly and have a good slip resistance and texture. The resulting powder compositions have many and diverse cosmetic applications, including use as foundations, eye shadow, blushes, skincare preparations, mascaras, creams, gels, and lotions.

Example 4

Foaming Body Scrub

A foaming body scrub comprising polylactic acid (PLA) with a maximum particle size of 840 microns and a maximum mesh size of 20 and the ingredients listed below was made according to the following:

| Product Name | INCI Name | % W/W | Supplier |
|---|---|---|---|
| Phase A | | | |
| Deionized water | Water | 51.20 | N/A |
| Carbopol Ultrez 20 | Carbomer | 0.60 | The Lubrizol Corporation (Wickliffe, Ohio) |
| Phase B | | | |
| Propylene Glycol | Propylene Glycol | 3.50 | Many |
| Germaben II | Propylene Glycol, Diazolidinyl Urea, Methylparaben, Propylparaben | 1.00 | International Specialty Products (Wayne, New Jersey) |
| Phase C | | | |
| Protachem ES-2 | Sodium Laureth Sulfate | 21.00 | Protameen Chemicals Inc. (Totowa, NJ) |
| Proteric CAB-LC | Cocamidopropyl Betaine | 7.00 | Protameen Chemicals Inc. (Totowa, NJ) |
| Protasorb L-20 | Polysorbate 20 | 1.50 | Protameen Chemicals Inc. (Totowa, NJ) |
| Protamide CME | Cocamide MEA | 3.50 | Protameen Chemicals Inc. (Totowa, NJ) |
| Phase D | | | |
| Deionized Water | Water | 3.00 | N/A |
| Disodium EDTA | Disodium EDTA | 0.05 | Many |
| Phase E | | | |
| Triethanolamine 99% | Triethanolamine | 0.65 | Many |
| Phase F | | | |
| EcoScrub 20PC | Polylactic acid | 7.00 | Micro Powders, Inc. (Tarrytown, NY) |

First, the Phase A solution is created by gentling sprinkling in the Carbopol Ultrez 20 on the surface of warm deionized water in a large vessel. (Heat the water to approximately 40° C.). Wait until the polymer has completely wetted out and then begin gentle mixing of the solution using any conventional mixing technique or apparatus known by those skilled in the art for 10 minutes. While the Phase A solution mixes, the Phase B solution is created. In a separate vessel, the Phase B materials are combined. Once the Phase A solution has mixed for ten minutes the Phase B solution is added to the Phase A solution. The combined solution (Phase AB) is then mixed until a homogeneous solution is created.

Once the Phase AB solution is homogeneous, the ingredients listed for Phase C are added individually and in the order listed above by a slow continuous mixing with a kitchen aid blender. It is important to make sure each ingredient is completely dispersed before beginning to add the next ingredient listed for Phase C.

In a separate vessel the Phase D solution is created by adding the listed ingredient by a slow continuous mixing process until completely dispersed. Phase D is then added to main batch which contains Phase A, B and C. The Phase E ingredient is then added to the batch and the pH is adjusted to 6.0-6.5 with TEA 99% component. The combined solution is then mixed until uniform. Then the Phase F is added slowly and again the solution is mixed until uniform.

The polylactic acid (PLA) used in the above formulation has a maximum particle size of 840 microns and a mesh size of 20 as measured using the ASTM E11 test method and an Alpine Sieve.

The resulting foaming body scrub is environmentally friendly and has the same high performance as body scrubs made with synthetic polymer particles. The resulting scrub composition has many and diverse cosmetic applications, including use as soap scrubs, foot scrubs, exfoliating face scrub, body scrubs, creams, liquids, gels and lotions.

Example 5

Foaming Body Scrub

A foaming body scrub comprising polylactic acid (PLA) with a maximum particle size of 297 microns and a maximum mesh size of 50 and the ingredients listed below was made according to the following:

| Product Name | INCI Name | % W/W | Supplier |
|---|---|---|---|
| Phase A | | | |
| Deionized water | Water | 51.20 | N/A |
| Carbopol Ultrez 20 | Carbomer | 0.60 | The Lubrizol Corporation (Wickliffe, Ohio) |
| Phase B | | | |
| Propylene Glycol | Propylene Glycol | 3.50 | Many |
| Germaben II | Propylene Glycol, Diazolidinyl Urea, Methylparaben, Propylparaben | 1.00 | International Specialty Products (Wayne, New Jersey) |
| Phase C | | | |
| Protachem ES-2 | Sodium Laureth Sulfate | 21.00 | Protameen Chemicals Inc. (Totowa, NJ) |
| Proteric CAB-LC | Cocamidopropyl Betaine | 7.00 | Protameen Chemicals Inc. (Totowa, NJ) |
| Protasorb L-20 | Polysorbate 20 | 1.50 | Protameen Chemicals Inc. (Totowa, NJ) |
| Protamide CME | Cocamide MEA | 3.50 | Protameen Chemicals Inc. (Totowa, NJ) |
| Phase D | | | |
| Deionized Water | Water | 3.00 | N/A |
| Disodium EDTA | Disodium EDTA | 0.05 | Many |
| Phase E | | | |
| Triethanolamine 99% | Triethanolamine | 0.65 | Many |
| Phase F | | | |
| EcoScrub 50PC | Polylactic acid | 7.00 | Micro Powders, Inc. (Tarrytown, NY) |

First, the Phase A solution is created by gentling sprinkling in the Carbopol Ultrez 20 on the surface of warm deionized water in a large vessel. (Heat the water to approximately 40° C.). Wait until the polymer has completely wetted out and then begin gentle mixing of the solution using any conventional mixing technique or apparatus known by those skilled in the art for 10 minutes. While the Phase A solution mixes, the Phase B solution is created. In a separate vessel, the Phase B materials are combined. Once the Phase A solution has mixed for ten minutes the Phase B solution is added to the Phase A solution. The combined solution (Phase AB) is then mixed until a homogeneous solution is created.

Once the Phase AB solution is homogeneous, the ingredients listed for Phase C are added individually and in the order listed above 1 by a slow continuous mixing with a CBM Mixer (6 qt, tumble speed 35, impeller speed 3500) for 1 minute until evenly dispersed. until evenly dispersed.

It is important to make sure each ingredient is completely dispersed before beginning to add the next ingredient listed for Phase C.

In a separate vessel the Phase D solution is created by adding the listed ingredient by a slow continuous mixing process until completely dispersed. Phase D is then added to main batch which contains Phase A, B and C. The Phase E ingredient is then added to the batch and the pH is adjusted to 6.0-6.5 with TEA 99% component. The combined solution is then mixed until uniform. Then the Phase F is added slowly and again the solution is mixed until uniform.

The polylactic acid (PLA) used in the above formulation has a maximum particle size of 297 and a mesh size of 50 mesh as measured using the ASTM E11 test method on an Alpine Sieve.

The resulting foaming body scrub is environmentally friendly and has the same high performance as body scrubs made with synthetic polymer particles. The resulting scrub composition has many and diverse cosmetic applications, including use as soap scrubs, foot scrubs, exfoliating face scrub, body scrubs, creams, liquids, gels and lotions.

An advantage of the compositions of the present invention is that the compositions are composed of natural polymers as opposed to a synthetic polymers. This is particularly desirable since the cosmetic compositions that can be created with the compositions of the present invention are for use on the human body. The compositions of the present invention and the cosmetic compositions created therefrom are ideally suited for use at home as well as at a salon or a spa.

The subsequent use of the powder and powder compositions of the invention depends on the desired aim and on the active agents which may be present. It can be used in particular to care for, cleanse, remove make-up from, make up and/or treat the human skin, scalp and/or mucous membranes.

Thus, another subject of the present invention is a cosmetic process to care for, cleanse, remove make-up from, make up and/or treat the skin, mucous membranes and/or the scalp, comprising the application of a powder as defined above to the skin, mucous membranes and/or the scalp.

Another subject of the invention is the use of the powder as defined above for the preparation of a composition intended to care for, cleanse, remove make-up from, make up and/or treat the skin, the scalp and/or mucous membranes.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements.

Obviously additional modifications and variations of the present invention are possible in light of the above teachings. It is therefore to be understood that within the scope of the appended claims, the invention may be practiced otherwise than as specifically described herein.

The invention claimed is:

1. A composition for topical application comprising:
   (a) from about 1% to about 30% by weight of a micronized polylactic acid (PLA) wherein the micronized polylactic acid comprises greater than 50% irregular shaped particles with a rough topography; and
   (b) one or more cosmetic powder base components selected from the group consisting of pigments, matte finishing agents, light scattering agents, fillers and binders, and mixture thereof;
   wherein said composition is in the form of a powder.

2. The composition of claim 1 wherein the micronized polylactic acid (PLA) polymer has a particle size from about 0.1 microns to about 44 microns.

3. The composition of claim 1 wherein the micronized polylactic acid (PLA) polymer is present in an amount from about 5% to about 10% by weight.

4. The composition according to claim 1 wherein the binder is a wax present in amount from about 1% to about 30% by weight.

5. The composition of claim 1 further comprising an additive present in an amount from about 0.5% to about 20% by weight.

6. A composition for topical application comprising:
   (a) from about 1% to about 10% by weight of a micronized polylactic acid (PLA) having irregular shaped particles with a rough topography; and
   (b) a cosmetically acceptable agent; wherein said composition is in the form of a cosmetic scrub.

7. The composition of claim 6 wherein the micronized polylactic acid (PLA) has a particle range from about 140 mesh to about 14 mesh.

8. The composition according to claim 6 further comprising a surfactant present in amount from about 1% to about 60% by weight.

9. The composition according to claim 6 wherein the cosmetically acceptable agent is present in an amount from about 5% to about 90% by weight.

10. A method of cleansing and/or removing makeup from the skin, the eyes, the scalp and/or the hair comprising: applying the composition of claim 6 to the skin, the eyes, the scalp and/or the hair thereby cleansing and/or removing make-up from the skin, the eyes, the scalp and/or the hair.

11. A method of preparing a cosmetic composition comprising:
   (a) preparing a biodegradable polymer powder by micronizing the polymer pellet by mechanical grinding or air jet milling; and
   (b) adding about 3 to 20 weight percent, based upon the total weight of the composition, of the aggregate with a cosmetically acceptable carrier wherein the micronized biodegradable polymer has an irregular shaped particles with a rough topography.

12. A method of treating keratin materials, comprising:
   applying the composition of claim 6 to the skin, thereby removing sebum and dead skin cells from the skin.

13. A method caring for, cleaning, removing make-up from and/or coloring the skin, mucous membranes and/or scalp, comprising applying the composition of claim 6 to the skin, mucous membranes and/or scalp.

14. A cosmetic mask, comprising: an applied composition of claim 6 as a mask on the skin of the face.

15. A method of treating skin, mucous membranes or the scalp, comprising:
   applying the composition of claim 6 to the skin, mucous membranes or the scalp.

16. A powder composition suitable for use in a cosmetic composition, comprising at least one micronized biodegradable polymer wherein the at least one micronized biodegradable polymer comprises greater than 50% irregular shaped particles with a rough topography.

17. The composition of claim 16 wherein the at least one micronized biodegradable polymer comprises greater than 75% irregular shaped particles with a rough topography.

18. The composition of claim 16 wherein the at least one micronized biodegradable polymer comprises greater than 90% irregular shaped particles with a rough topography.

19. The composition according to claim 16 in which the at least one micronized biodegradable polymer is present in an amount from 0.5% to 100% % by weight.

20. The composition according to claim 16 wherein the at least one micronized biodegradable polymer is polylactic acid (PLA).

21. The composition according to claim 20 wherein the polylactic acid (PLA) has a mean particle size from about 1 to 44 microns.

22. The composition according to claim 20 wherein the polylactic acid (PLA) has a maximum particle size from about 120 mesh to 20 mesh.

23. The composition according to claim 20 wherein the polylactic acid (PLA) has a mean particle size from about 80 to 500 microns.

24. The composition according to claim 16 further comprising an additive in the amount from about 0.1% to 99.5% by weight.

25. The composition according to claim 24 wherein the additive comprises a binder or wax in an amount from about 1% to 30% by weight.

26. A composition comprising:
   (a) at least one micronized biodegradable polymer having greater than 50% irregular shaped particles with a rough topography; and
   (b) one or more additives selected from the group consisting of pigments, dyes, matte finishing agents, light scattering agents, fillers and binders, and mixture thereof.

27. The composition according to claim 26 wherein the biodegradable polymer is selected from the group consisting of polylactic acid (PLA), polyhydroxyalkanoate and polycaprolactone.

28. The composition according to claim 27 wherein the biodegradable polymer has a mean particle size from about 1 to 300 microns.

29. The composition according to claim 26 wherein the additive is present in an amount from about 0.1% to 99.5% by weight.

30. The composition according to claim 29 wherein the additive comprises a pigment or dye in an amount from about 0.5% to 50% by weight.

31. A powder composition suitable for use in a cosmetic composition comprising a micronized biodegradable polymer having irregular shaped particles with a rough topography selected from the group consisting of polylactic acid, polyhydroxyalkanoate and polycaprolactone wherein the at least one micronized biodegradable polymer comprises greater than 50% irregular non-uniform granular particles.

* * * * *